(12) United States Patent
Rankin

(10) Patent No.: US 9,074,948 B2
(45) Date of Patent: Jul. 7, 2015

(54) METHOD FOR INDIRECT FOOD TEMPERATURE MEASUREMENT

(71) Applicant: John Rankin, Circleville, OH (US)

(72) Inventor: John Rankin, Circleville, OH (US)

(73) Assignee: Connectivity Systems Incorporated, Williamsport, OH (US)

( * ) Notice: Subject to any disclaimer, the term of this patent is extended or adjusted under 35 U.S.C. 154(b) by 0 days.

(21) Appl. No.: 13/655,826

(22) Filed: Oct. 19, 2012

(65) Prior Publication Data

US 2013/0294477 A1 Nov. 7, 2013

Related U.S. Application Data

(60) Provisional application No. 61/548,992, filed on Oct. 19, 2011.

(51) Int. Cl.
| | |
|---|---|
| *G01K 17/00* | (2006.01) |
| *A47J 27/10* | (2006.01) |
| *G01K 13/00* | (2006.01) |
| *A47J 36/32* | (2006.01) |

(52) U.S. Cl.
CPC *G01K 13/00* (2013.01); *A47J 36/32* (2013.01)

(58) Field of Classification Search
CPC ............................ A47J 31/545; A47J 37/1266
USPC ........... 374/100, 141, 45, 4, 30–39, 10–12, 1, 374/29; 99/325, 326, 328, 331, 403, 324, 99/DIG. 10, 342, 467, 472, 485; 219/620, 219/627, 667, 730, 731, 660, 386, 524, 219/DIG. 10
See application file for complete search history.

(56) References Cited

U.S. PATENT DOCUMENTS

| | | | | | |
|---|---|---|---|---|---|
| 1,379,370 | A | * | 5/1921 | Szatmary | ...................... 451/369 |
| 1,768,148 | A | * | 6/1930 | Reardon | .................... 126/374.1 |
| 3,279,451 | A | * | 10/1966 | Oehring | ...................... 126/21 A |
| 4,102,330 | A | * | 7/1978 | Hutchinson | ................ 126/374.1 |
| 4,135,003 | A | * | 1/1979 | Mohwinkel | ................... 426/412 |
| 4,258,695 | A | * | 3/1981 | McCarton et al. | ......... 126/375.1 |
| 4,320,285 | A | * | 3/1982 | Koether | ........................ 219/497 |
| 4,506,598 | A | * | 3/1985 | Meister | .......................... 99/330 |
| 4,848,921 | A | * | 7/1989 | Kunze | ............................. 374/11 |
| 5,123,337 | A | * | 6/1992 | Vilgrain et al. | .................. 99/483 |
| 5,542,344 | A | * | 8/1996 | Koether et al. | ................. 99/330 |
| 5,613,423 | A | * | 3/1997 | Polster | ............................ 99/330 |
| 5,803,357 | A | * | 9/1998 | Lakin | .......................... 236/78 B |
| 5,805,767 | A | * | 9/1998 | Jouas et al. | ................... 392/373 |
| 5,827,556 | A | | 10/1998 | Maher, Jr. | |

(Continued)

FOREIGN PATENT DOCUMENTS

| | | | |
|---|---|---|---|
| DE | 102009042304 A1 | | 3/2011 |
| JP | 58062564 A | * | 4/1983 |

*Primary Examiner* — Gail Kaplan Verbitsky
(74) *Attorney, Agent, or Firm* — Standley Law Group LLP

(57) ABSTRACT

A system and method for the preparation of food, but without the requirement of weight, time and/or temperature probe usage to determine the point at which the food has completed preparation. The exemplary embodiments provide a process where the food can be cooked without the requirements of calculation or temperature probes. The described process allows the process operator to be informed when the cooking process has completed, without regard to the size, shape, weight, density, or amount of materials to be prepared. The energy required to maintain the temperature of a water bath is compared to the energy required to maintain the temperature once a food item has been placed within the water bath.

14 Claims, 4 Drawing Sheets

(56) References Cited

U.S. PATENT DOCUMENTS

| | | | |
|---|---|---|---|
| 6,246,831 B1* | 6/2001 | Seitz et al. | 392/486 |
| 6,849,830 B2* | 2/2005 | Damiano et al. | 219/386 |
| 6,907,680 B2* | 6/2005 | Mariotti | 34/486 |
| 7,053,342 B2* | 5/2006 | Kim | 219/494 |
| 7,432,477 B2* | 10/2008 | Teti | 219/492 |
| 7,501,608 B2* | 3/2009 | Hallgren et al. | 219/705 |
| 8,609,168 B2* | 12/2013 | Ceravalls Pujol et al. | 426/231 |
| 8,690,886 B2* | 4/2014 | Fedorov et al. | 606/99 |
| 2003/0102303 A1* | 6/2003 | Clothier et al. | 219/627 |
| 2004/0005489 A1* | 1/2004 | Wakabayashi et al. | 429/24 |
| 2004/0168685 A1* | 9/2004 | Lange | 126/351.1 |
| 2006/0151473 A1* | 7/2006 | Su | 219/506 |
| 2007/0095819 A1* | 5/2007 | Kuban et al. | 219/512 |
| 2008/0037965 A1* | 2/2008 | De Luca | 392/416 |
| 2010/0145787 A1* | 6/2010 | Ohman et al. | 705/14.31 |
| 2011/0031236 A1* | 2/2011 | Ben-Shmuel et al. | 219/620 |
| 2011/0108547 A1* | 5/2011 | Rosenbloom et al. | 219/626 |
| 2011/0185915 A1 | 8/2011 | Eades et al. | |
| 2012/0010845 A1* | 1/2012 | Bohan et al. | 702/130 |
| 2012/0230661 A1* | 9/2012 | Alhilo | 392/441 |
| 2013/0048625 A1* | 2/2013 | Sladecek et al. | 219/494 |
| 2013/0183423 A1* | 7/2013 | Todys et al. | 426/418 |

* cited by examiner

METHOD FOR INDIRECT FOOD TEMPERATURE MEASUREMENT

CROSS-REFERENCE TO RELATED APPLICATIONS

This application claims priority to U.S. Application No. 61/548,992, filed on Oct. 19, 2011, which is herein incorporated by reference in its entirety.

TECHNICAL FIELD

Exemplary embodiments of the present invention are in the field of food preparation and more particularly in the field of improved temperature measurement during the preparation of food.

BACKGROUND

Conventional food preparation through heating has many inefficiencies, including the risk of undercooking, overcooking, or burning the food; all of which can lead to significant waste. Much of the effort that goes into preparing foods, especially meats, is directed to achieving an accurate temperature. In the case of foods such as chicken the accurate temperature is a necessity as illness can result from allowing people to consume the undercooked meat. However, conventional temperature measurement requires puncturing the outer layers of the flesh of the food to insert a thermometer in order to get an accurate measurement of the interior temperature of the food, to ensure thorough and complete cooking.

Sous-vide (under vacuum) cooking is a more recent development in food preparation. Sous-vide preparation involves placing a portion of food and associated spices or marinades in a flexible package and removing the air from the package and sealing the food under vacuum. The package is then placed in a bath of predetermined temperature for a set amount of time. Advantages of this type of preparation include the fact that overcooking of the food is very difficult. In conventional food preparation the cooking surface is much hotter than the desired temperature of the food—thus the food continues to increase in temperature and it is up to the food preparer to determine when the appropriate temperature has been achieved. Whereas in sous-vide preparation the bath is kept close to the desired food temperature and the food must simply remain in the bath long enough to reach the bath temperature, then the food will cease to increase in temperature as there is no thermodynamic motivation to drive more energy into the food. Thus, with sous-vide preparation accurate temperatures are achieved without the risk of overcooking the food. However, with the risks of, for example, serving undercooked food to patrons, vendors who serve sous-vide prepared dishes continue to check the internal temperature of their foods in order to prevent serving underprepared food. This often involves puncturing the sealed package and inserting a thermometer, much as before. Although necessary, this practice reduces the quality of the served food and, should the food be found to be undercooked, reduces the efficiency of reheating the food to achieve the desired temperature.

Conventional sous-vide cooking technique requires a method relating to the timing and the determining of when the contained items have reached its optimal temperature. Currently, there are only two methods in use to determine when the object to be cooked has completely its operation:

The size, shape, weight, density and starting temperature is examined in order to determine the amount of time necessary to reach the desired temperature. The sealed container is then lowered into the water bath and held there until the calculated amount of time has elapsed.

A temperature probe is inserting into the object that is to be heated, in order to measure the temperature during the cooking process and determine with the cooking process has completed. Since the object to be cooked in contained within a vacuum sealed container, this temperature probe must not be inserted in such a way as to disturb the vacuum seal of the container.

These two methods for determining cooking time present several issues:

The time calculation requires a great deal of careful and skilled calculation in order to properly estimate the amount of necessary time. Since this issue can be quite difficult, depending upon the shape of the object, the sous-vide process operator can overcome this issue, by extending the time longer than truly necessary. While this solution produces reasonable results, it has the disadvantage of affecting food flavor and tying up value resources that can be used for further food processing.

The temperature probe can be problematic, as the contained object must continue to be held under a vacuum seal while the probe is inserted. While that can be accomplished by the use of an external air tight material, the technique is highly prone to error. Furthermore, the use of several temperature probes within the same sous-vide water bath creates a greater likelihood of vacuum failure.

SUMMARY

Disclosed embodiments comprise a system designed to cook food using the sous-vide style of cooking, but without the requirement of weight, time and/or temperature probe usage to determine the point at which the food has completed cooking. The exemplary embodiments provide a process where the food contained within a vacuum sealed container can be cooked without the requirements of calculation or temperature probes. The described process allows the sous-vide process operator to be informed with the cooking process has completed, without regard to the size, shape, weight, density, beginning temperature or amount of materials to be cooked.

The proposed sous-vide processor uses the careful monitoring of the consumption of energy in order to determine with the cooking process has completed. As a sous-vide processing system consists of a temperature controlled water bath, into which a sealed container is placed, the sous-vide cooking process provides an ideal environment for controlled energy monitoring. By monitoring the amount of additional energy necessary to bring the additional contained object to the equal temperature of the water bath, it is possible to exactly determine the end of this process, by the elimination of any further energy requirements.

The amount of energy necessary to bring ten gallons of water, at a particular altitude, to 165° F., is greater than the amount of energy necessary to maintain that same volume of water at a constant temperature of 165° F. By carefully measuring the amount of energy necessary to maintain the temperature of the water bath as a base line of energy use can be established. Let us refer to this base line of energy use as eBase. Where eBase is the amount of energy necessary to maintain the water bath at a fixed and predetermined temperature.

Once a vacuum sealed object is inserted within the sous-vide bath, the amount of energy necessary within the system will rise above the amount determined to be eBase. This additional amount of energy will be necessary until the inserted object has itself reached a temperature that is equal to that of sous-vide water bath. At this point in the process the energy necessary for the system as a whole will once again be measurable as a value equal to eBase. Therefore, the inserted object has completed the heating process and is ready for extraction.

Disclosed embodiments describe a method for the accurate determination of food temperature. The method includes providing a water bath of known capacity and temperature. The water bath includes a means for determining the temperature of the water, a controller for controlling a heating element to achieve a predetermined temperature. Raising the temperature of the bath to the predetermined temperature. Determining the amount of energy required to maintain the bath at the predetermined temperature, and signaling when the amount of energy has been determined.

Disclosed embodiments describe a method for the accurate and non-invasive measurement of the temperature of food during preparation, the method comprising the steps of: providing a water bath, the water bath comprising: an energy input, a basin, a thermometer adapted to measure the temperature of the basin, a heating element in electrical communication with the energy input and in thermal communication with the basin, the basin comprising a watertight basin with a bottom and four sidewalls extending upward from the bottom; providing a programmable controller, the controller adapted to receive predetermined temperature input from a user and to control the temperature of the water basin by turning the heating element on or off, and adapted to measure the energy drawn by the heating element during operation through the energy input; the controller receiving temperature input from the thermometer and transmitting a signal to the heating element directing it to turn on if the temperature input is below the predetermined temperature or directing it to turn off if the temperature input is at the predetermined temperature; measuring an eBase for the basin; storing the value of the eBase at the controller; measuring the eOperation of the basin; transmitting a signal when eOperation is substantially equal to eBase.

Disclosed embodiments describe an apparatus for the indirect measurement of the temperature of a food item. The apparatus includes a watertight basin comprising a bottom and four sidewalls extending upwards from the bottom; a heating element adapted to increase the temperature of the basin; an energy input means for providing energy to the heating element and in electrical communication with the heating element; a thermostat in thermal communication with the basin; and a programmable controller. The controller is adapted to receive: predetermined temperature input from a user, current temperature measurements from the thermostat, and is adapted to control the heating element in response to the temperature measurements, further adapted to measure the energy drawn by the heating element while heating the basin, and further adapted to transmit a signal in response to the measured energy draw.

BRIEF DESCRIPTION OF THE DRAWINGS

A better understanding of the exemplary embodiments of the invention will be had when reference is made to the accompanying drawings, wherein identical parts are identified with identical reference numerals, and wherein.

DETAILED DESCRIPTION

Figure 1:
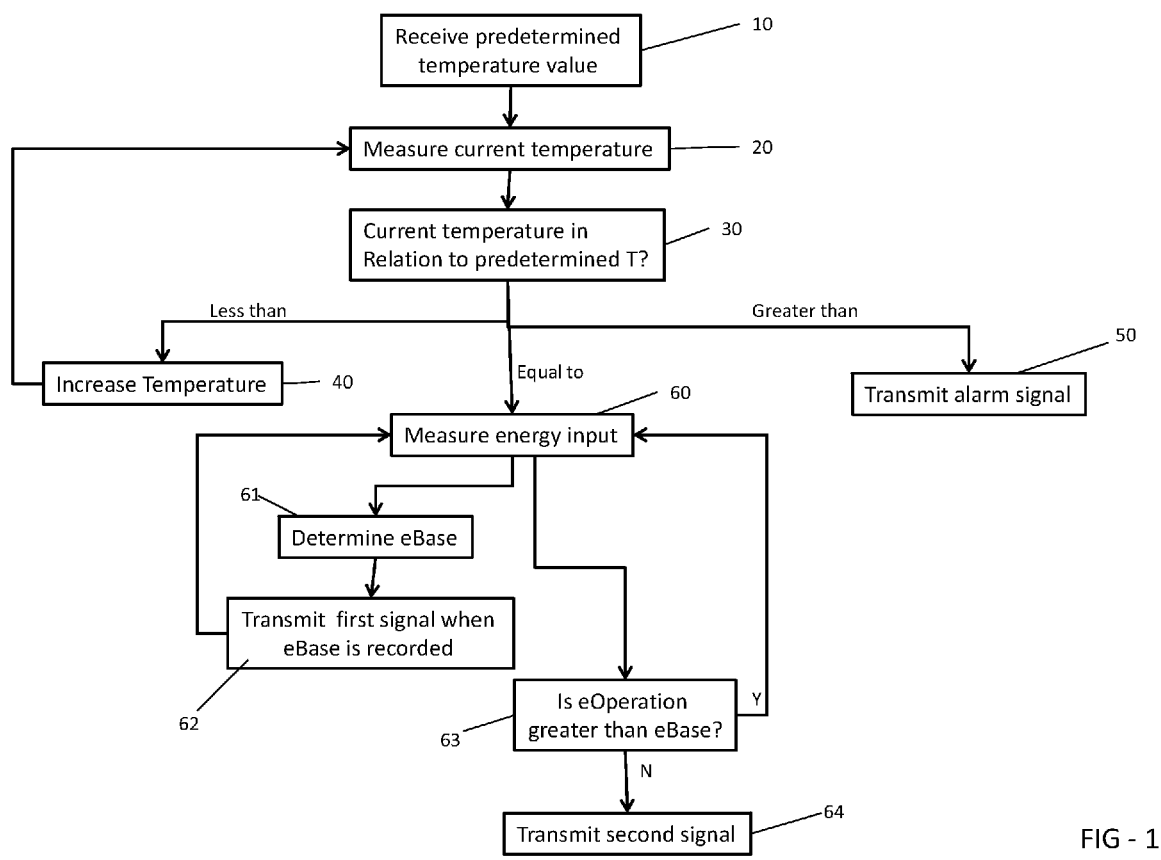
FIG. 1 is a flowchart illustrating the steps comprising an embodiment of the present invention.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The exemplary embodiments provide a process where the food contained within a vacuum sealed container can be prepared without the requirements of calculation, temperature probes or the intervention of a cooking professional. The disclosed embodiments allow the sous-vide process operator to be informed as to when the cooking process has completed, without regard to the size, shape, weight, density, beginning temperature or amount of materials to be cooked.

The proposed sous-vide food preparation apparatus and method uses the careful monitoring of the consumption of energy in order to determine when the food preparation process has been completed. As a sous-vide processing system consists of a temperature controlled water bath, into which a sealed container is placed, the sous-vide cooking process provides an ideal environment for controlled energy monitoring. By monitoring the amount of additional energy necessary to bring the contained object to the temperature of the water bath, it is possible to determine the end of this process by the elimination of any further energy requirements.

The amount of energy necessary to bring ten gallons of water, at a particular altitude, to 165° F., is greater than the amount of energy necessary to maintain that same volume of water at a constant temperature of 165° F. By carefully measuring the amount of energy necessary to maintain the temperature of the water bath as base line of energy consumption—can be established. Let us refer to this base line of energy use as eBase. Where eBase is the amount of energy necessary to maintain the sous-vide basin at a fixed and predetermined temperature.

Once a vacuum sealed object is inserted within a basin, the amount of energy required by the system to maintain the predetermined temperature will rise above the amount determined to be eBase. This additional amount of energy will be necessary until the inserted object has itself reached a temperature that is equal to the predetermined temperature. At this point in the process the energy necessary for the system as a whole will once again be measurable as a value equal to eBase. Therefore, the inserted object has completed the heating process and is ready for extraction.

As a practical example, let us once again examine the process of cooking a piece of chicken. The sous-vide basin is brought to 165° F. and a value for eBase may be determined based on the voltage required to maintain this temperature. The vacuum sealed chicken is then lowered into the basin. The amount of millivolts necessary to maintain the basin at 165° F., will begin to increase above the amount established as eBase, and shortly reach a peek amount above eBase. It takes the chicken a period of time for the entire object to reach the temperature of 165° F. During the time necessary for this cooking process to occur, the amount of millivolts above eBase will continue to fall, until once again the amount of millivolts consumed by the system has reached the amount determined to be eBase. At this point in time the chicken has been completely cooked and can be served.

Turning to the drawings for a better understanding:

FIG. 1 shows a flowchart illustrating the steps comprising an embodiment of the present invention. The water bath controller receives the input of the predetermined temperature of the basin at an input means 10. Upon measuring the temperature of the basin 20, the controller then directs the heating element to increase the temperature of the basin until the predetermined temperature has been reached 40. Once the predetermined temperature has been achieved the amount of energy required to maintain the predetermined temperature of the bath is measured by the controller 60. This amount of energy is recorded as eBase 61. The controller then transmits a signal acknowledging that the predetermined temperature has been achieved and eBase has been determined 62. Food is then placed in the bath causing the amount of energy required to maintain the predetermined temperature to increase. The controller continues to measure the energy needs of the bath and to signal the heating element to heat the basin when necessary 63. When the energy returns to the eBase, the controller notifies the user that the food has reached the desired temperature 64. The controller may provide user notifications through an audible alarm or tone or though a visual indication on the display 136 or a simple light which illuminates. The controller may also provide notifications to the user through a transmission to a wireless device.

Figure 2:
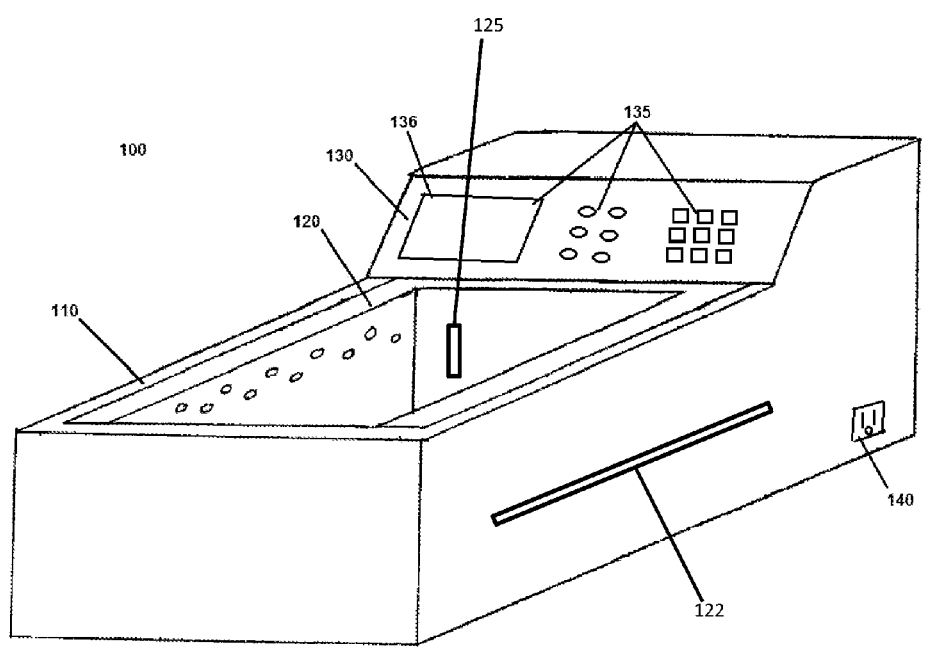
FIG. 2 is a perspective view of an exemplary water bath.

FIG. 2 is a diagram of a water bath and controller in accordance with an embodiment of the present invention. The water bath 100 comprises a housing 110 around a basin 120, the basin defined by a bottom and four upwardly extending sidewalls. The sidewalls and/or the bottom are in thermal communication with a heating element 122 and a thermostat 125. The heating element receives energy from an energy input 140 and provides heat to increase the temperature of the water and any food deposited into the basin to a predetermined temperature. The bath also includes a controller 130 within the housing. The controller 130 is preferably in electrical communication with a user interface 135, the heating element 122, and the thermostat 125.

The controller 130 is preferably adapted to receive electrical input from the thermostat 125 regarding the current temperature of the basin. The controller 130 is preferably also adapted to receive input from the user interface 135 as to the desired temperature of the basin and to monitor the energy provided by the heating element 122 and the temperature measured by the thermostat 125, to control the temperature of the basin via the heating element and to transmit signals corresponding to operation of the bath. Optionally, the controller also receives a signal from a water level detection means positioned along a sidewall of the basin. The controller 130 is adapted to transmit a signal to the heating element directing it to increase the temperature or to maintain the current temperature, in response to measurements from the thermostat 125. The controller may comprise, but is not limited to any one of the following: EPROM, EEPROM, microprocessor, RAM, CPU, or any form of software driver capable of reading electrical signals from the user interface and thermostat, controlling/measuring the power sent to the heating element, and controlling the means for notifying the user.

Figure 3:
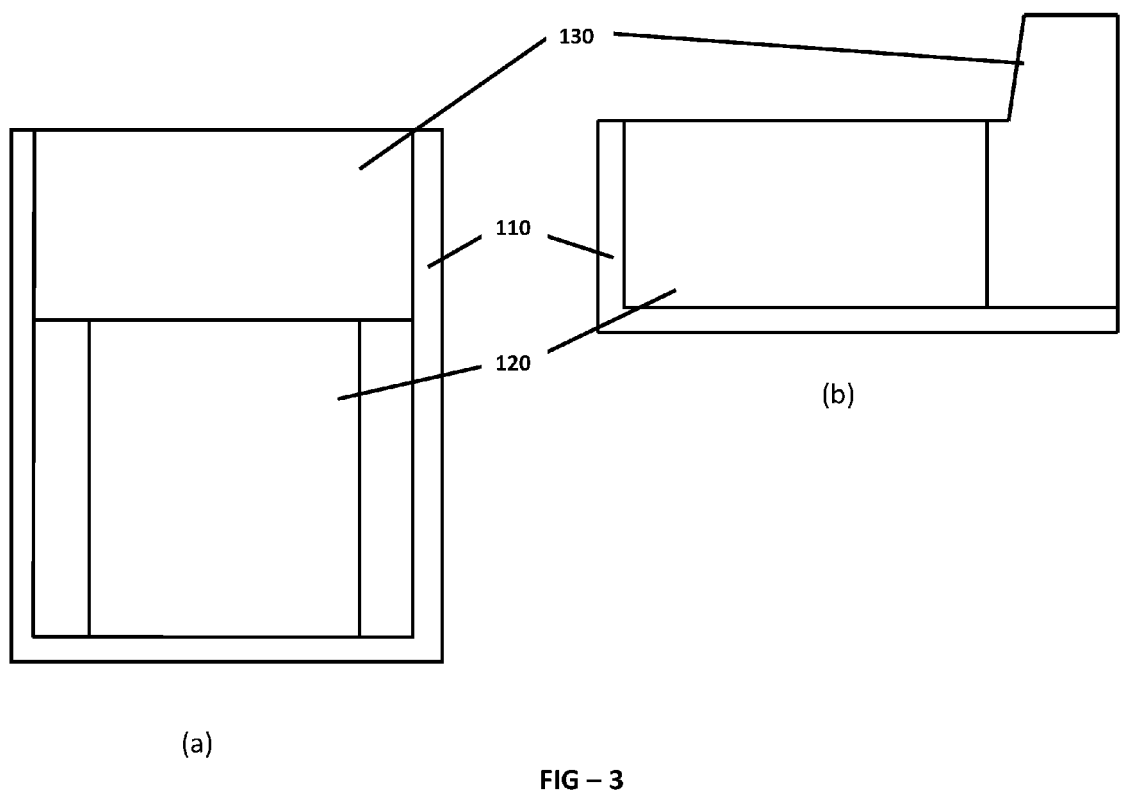
FIG. 3a is a top view of an exemplary water bath.
FIG. 3b is a cross-sectional side view of an exemplary water bath.

FIGS. 3a and 3b show top and side cross-sectional views of a water bath in accordance with an embodiment of the present invention. The water bath is adapted to perform the method described herein. The figures show the relative placement of the housing 110, the basin 120 and the controller 130.

Figure 4:
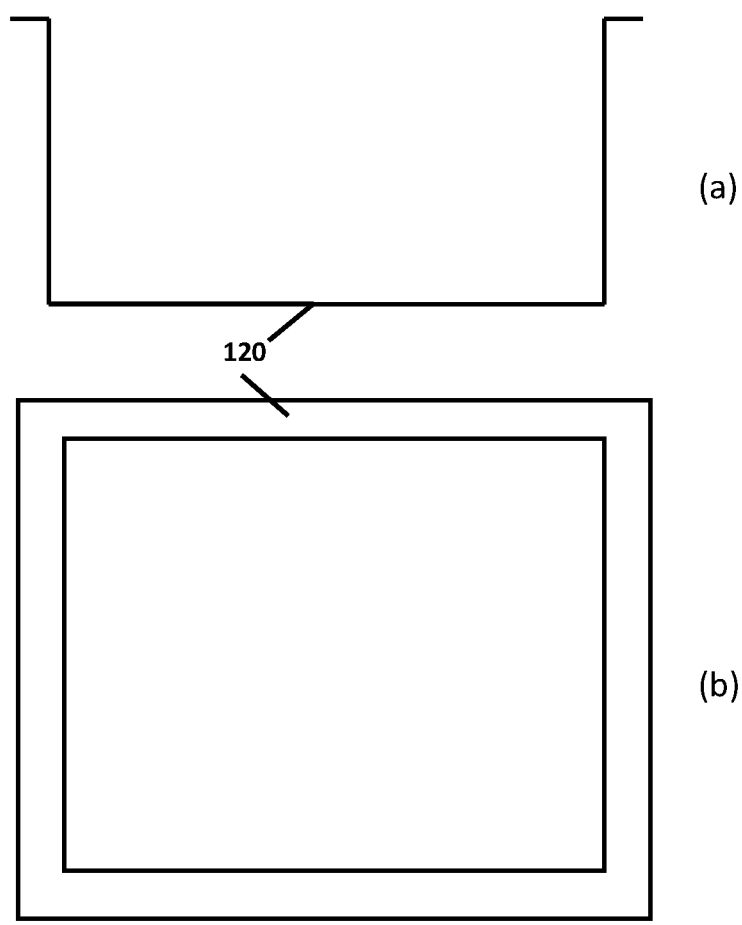
FIG. 4a is a cross-sectional side view of an exemplary basin.
FIG. 4b is a top view of an exemplary basin.

FIGS. 4a and 4b shows cross-sectional and top views of a basin 120 according to an embodiment of the present invention.

The controller 130 monitors and controls the holding and preparation timing of the water bath. In an embodiment, the controller 130 comprises a processing unit with memory storing a plurality of predetermined temperature values and times, which may be selected and/or edited by a user via the user interface 135. The water bath further comprises a display 136 on an exterior surface of the water bath in communication with the controller 130 for providing feedback regarding operation of the bath including user prompts, displaying recent commands provided to the controller via the user interface 135. Optionally, the user interface 135 comprises keys for navigating through the display 136 and possibly an alphanumeric keyboard, a multi-function timing device, and a parameter storage device.

During operation, the controller receives input regarding a desired, predetermined temperature via the user interface 135 which is in electrical communication with the controller 130. This input may be accomplished by providing the water bath with preprogrammed buttons corresponding to predetermined temperature values or by providing the user interface 135 with manual temperature selection input. In an embodiment, the predetermined temperature values correspond to a desired level of doneness for a food item or to a necessary temperature for safe serving of food items such as chicken to avoid the service of undercooked food. Optionally, the predetermined temperature settings correspond to, for example, FDA guidelines for the safe preparation of food items.

Once the temperature input is received by the controller 130, it directs the heating element 122 to increase the temperature of the basin or to maintain the temperature of the basin depending on the current temperature of the basin in relation to the predetermined temperature. In an embodiment, the controller 130 is adapted to transmit an alarm signal should the temperature recorded by the thermostat 125 be above the predetermined temperature. The controller 130 monitors the amount of energy drawn by the heating element 122 in response to its instructions. Once the basin achieves the predetermined temperature, the controller determines an eBase—the amount of energy drawn by the basin per unit of time in order to maintain the predetermined temperature. Once the controller 130 has determined the eBase, the controller 130 transmits a first signal acknowledging that it has determined the eBase. In response to the first signal, a food item is placed in the basin. The thermostat 125 may then return a lower temperature than the predetermined temperature and the controller 130 will preferably direct the heating element 122 to increase the temperature of the basin. This will then cause the amount of energy drawn by the bath to increase above eBase. This amount of energy drawn by the bath while heating a food item is the eOperation. The amount of energy drawn by the bath will remain above eBase until the food item reaches the predetermined temperature, at which point the eOperation will approximate eBase. Upon achieving eBase, the controller will then transmit a second signal, acknowledging that the desired temperature has been achieved. In a restaurant or food preparation environment, this signal will indicate that the food item is ready for further preparation or serving. Optionally, the user interface 135 includes an input for signaling the controller 130 that a food item has been placed in the basin.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosed embodiments and does not pose a limitation on the scope of the disclosed embodiments unless otherwise claimed. No language in the specification should be construed as indicating any non-claimed element essential to the practice of the disclosed embodiments or any variants thereof.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability Preferred embodiments of this invention are described herein, including the best mode known to the inventors for carrying out the invention(s). Of course, variations on the disclosed embodiments will become apparent to those of ordinary skill in the art upon reading the foregoing description. The inventors expect skilled artisans to employ such variations as appropriate, and the inventors intend for the invention(s) to be practiced otherwise than specifically described herein. Accordingly, this disclosure includes all modifications and equivalents of the subject matter recited in the claims appended hereto as permitted by applicable law. Moreover, any combination of the above described elements in all possible variations thereof is encompassed by the disclosed embodiments unless otherwise indicated herein or otherwise clearly contradicted by context.

Having shown and described an embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

What is claimed is:

1. A method for measuring the temperature of food during preparation by measuring energy, the method comprising the steps of:
   selecting a desired temperature for the food;
   heating a water bath until the water has reached the selected temperature;
   obtaining the energy required to maintain the water bath at the selected temperature as eBase;
   storing eBase;
   placing a food item into the water bath;
   maintaining the water bath at the selected temperature while storing the energy required to maintain the water bath at the selected temperature as eOperation;
   continuously comparing eOperation to eBase; and
   providing an indication to a user once eOperation is equal to eBase as an indication of the food temperature.

2. The method of claim 1 further comprising the step of:
   providing an indication to a user when eBase has been stored.

3. The method of claim 1 further comprising the step of:
   placing the food item into a vacuum sealed package prior to placing into the water bath.

4. A method for measuring the temperature of food during preparation by measuring energy, the method comprising the steps of:
   providing a basin, a thermostat adapted to measure the temperature of water within the basin, a heating element in thermal communication with the basin, and a controller in electrical communication with the thermostat, heating element, and a user interface;
   inputting a desired temperature value for the water at the user interface;
   causing the controller to direct the heating element to heat the water in the basin until the thermostat indicates that the desired temperature has been reached;
   measuring an eBase for the basin;
   storing the value of the eBase at the controller;
   transmitting a notification when eBase has been stored;
   placing a food item into the water bath;
   measuring an eOperation of the basin with the food item in the water basin; and
   transmitting a notification when eOperation is substantially equal to eBase as an indication of the food temperature.

5. The method of claim 4 wherein:
   the eBase is the amount of energy drawn by the heating element to keep the basin at the desired temperature.

6. The method of claim 4 wherein:
   eOperation is the amount of energy drawn by the heating element after a food item is placed in the basin while achieving the desired temperature.

7. The method of claim 4 wherein:
   the desired temperature corresponds to a temperature for a desired level of cooking of the food item.

8. The method of claim 4 wherein:
   the user interface includes preprogrammed buttons corresponding to desired temperatures.

9. An apparatus for measuring the temperature of food during preparation, comprising
   a basin containing a water bath;

a thermostat adapted to measure the temperature of the water;
a heating element in thermal communication with the basin;
a user interface adapted to accept a desired temperature from a user;
a means for notifying the user; and
a controller in electrical communication with the thermostat, heating element, user interface, and the means for notifying the user;
wherein the controller is adapted to
  receive a desired temperature from the user interface,
  direct the heating element to heat the basin until the water has reached the desired temperature,
  store the energy required to maintain the water at the desired temperature as eBase,
  once the food is placed within the water bath, direct the heating element to maintain the water at the desired temperature while storing the energy required to maintain the water at the desired temperature as eOperation,
  frequently compare eOperation to eBase, and
  initiate the means for notifying the user once eOperation is equal to eBase.

10. The apparatus of claim 9 wherein the controller comprises any one of the following:
EPROM, EEPROM, microprocessor, RAM, CPU, or software driver.

11. The apparatus of claim 9 further comprising:
a display in electrical communication with the controller.

12. The apparatus of claim 11 wherein:
the means for notifying the user comprises a visual notification on the display.

13. The apparatus of claim 9 wherein:
the means for notifying the user comprises an audible alarm.

14. The apparatus of claim 9 wherein:
the user interface contains a button corresponding to a pre-determined desired temperature.

* * * * *